United States Patent
Relenyi et al.

(10) Patent No.: US 10,472,266 B2
(45) Date of Patent: Nov. 12, 2019

(54) MULTIPLE USES OF AMINE SALTS FOR INDUSTRIAL WATER TREATMENT

(71) Applicant: AMSA, Inc., Auburn, MI (US)

(72) Inventors: Attila G Relenyi, Midland, MI (US); Anthony P Haag, Bozeman, MT (US)

(73) Assignee: AMSA, INC., Auburn, MI (US)

( * ) Notice: Subject to any disclaimer, the term of this patent is extended or adjusted under 35 U.S.C. 154(b) by 0 days.

(21) Appl. No.: 15/885,073

(22) Filed: Jan. 31, 2018

(65) Prior Publication Data

US 2018/0155226 A1 Jun. 7, 2018

Related U.S. Application Data

(62) Division of application No. 14/129,726, filed as application No. PCT/US2013/034250 on Mar. 28, 2013, now Pat. No. 9,919,941.

(60) Provisional application No. 61/616,786, filed on Mar. 28, 2012.

(51) Int. Cl.
| | |
|---|---|
| *C02F 5/14* | (2006.01) |
| *A01N 33/08* | (2006.01) |
| *C02F 1/50* | (2006.01) |
| *C02F 5/12* | (2006.01) |
| *C02F 1/68* | (2006.01) |
| *C02F 103/02* | (2006.01) |

(52) U.S. Cl.
CPC ............... *C02F 5/12* (2013.01); *A01N 33/08* (2013.01); *C02F 1/50* (2013.01); *C02F 1/683* (2013.01); *C02F 5/14* (2013.01); *C02F 2103/023* (2013.01); *C02F 2303/08* (2013.01); *C02F 2303/20* (2013.01)

(58) Field of Classification Search
CPC .................................................. C07C 233/89
See application file for complete search history.

(56) References Cited

U.S. PATENT DOCUMENTS

| | | | |
|---|---|---|---|
| 3,291,683 A | 12/1966 | Lamb | |
| 3,524,719 A | 8/1970 | Wolf | |
| 4,816,061 A * | 3/1989 | Walter, Jr. ............... | A01N 33/08 504/160 |
| 4,952,327 A | 8/1990 | Amjad | |
| 4,982,004 A | 1/1991 | Relenyi | |
| 5,025,038 A | 6/1991 | Relenyi | |
| 5,087,757 A | 2/1992 | Mariam | |
| 5,128,065 A | 7/1992 | Hollander | |
| 5,224,990 A * | 7/1993 | Vicenzi ................... | C08K 3/346 106/277 |
| 5,681,798 A | 10/1997 | Farng | |
| 5,777,167 A | 7/1998 | Gartner | |

(Continued)

FOREIGN PATENT DOCUMENTS

| | | |
|---|---|---|
| EP | 0266828 B1 | 5/1988 |
| EP | 1471131 A1 | 10/2004 |

(Continued)

*Primary Examiner* — Clare M Perrin
(74) *Attorney, Agent, or Firm* — Technology Law PLLC; Karen L. Kimble

(57) ABSTRACT

A method for treating in an industrial water treatment system for at least two of metal corrosion inhibition, scale inhibition, suspended matter dispersion, biocide efficacy, or biofilm removal/biofilm dispersion is taught by the use of at least one compound which is a salt derived from a thioamine or an oxyamine and an acid.

5 Claims, 9 Drawing Sheets

Problems Addressed by Compounds of Formula (I)

(56) References Cited

U.S. PATENT DOCUMENTS

| | | | |
|---|---|---|---|
| 6,183,649 B1 | 2/2001 | Fontana | |
| 6,260,561 B1 | 7/2001 | Gartner | |
| 2005/0147528 A1* | 7/2005 | Shim | A01N 59/00 422/37 |
| 2006/0228323 A1 | 10/2006 | Novelle | |
| 2009/0178587 A9 | 7/2009 | Nalepa | |
| 2010/0297207 A1 | 11/2010 | Kemp | |
| 2011/0073802 A1 | 3/2011 | Haag | |

FOREIGN PATENT DOCUMENTS

| | | |
|---|---|---|
| RU | 2010124805 | 12/2011 |
| WO | 2005014491 | 2/2005 |

* cited by examiner

MULTIPLE USES OF AMINE SALTS FOR INDUSTRIAL WATER TREATMENT

BACKGROUND OF THE INVENTION

Field of the Invention

This invention generally concerns industrial water treatment (IWT) systems where often many different conditions arise that require treatment such as corrosion inhibition, scale inhibition, suspended matter dispersion, microbial control, biofilm removal, and biofilm dispersion.

Description of Related Art

Water is used in industry for the transfer of heat in recirculating cooling water systems and production of steam in boilers. There is extensive use of cooling water in most major manufacturing processes to operate efficiently and safely, in commercial air conditioning, and even in domestic air conditioning. Also refineries, steel mills, petrochemical manufacturing plants, electric utilities and paper mills all rely heavily on equipment or processes that require efficient temperature control and often use cooling water to moderate the temperature. Thus these cooling water systems are important to maintain operation of these heat transfer needs in a wide variety of process systems.

Recirculating cooling water systems control temperatures by transferring heat from hot process fluids into cooling water. As this happens, the cooling water itself gets hot and must be cooled by evaporation or secondary chiller system (the water is run through a cooling area or has refrigeration exposure). Water lost in this process must be replaced by a fresh supply of cool water (i.e. makeup water). The makeup water contains dissolved minerals, suspended solids, debris, bacteria, and other impurities. As the water continues to circulate throughout the cooling water system, other contaminants begin to concentrate. The inorganic contaminants, such as scale and corrosion products, may form deposits on heat transfer surfaces and in piping. In addition, biofouling may result by formation of biofilms on surfaces due to growth of microorganisms. These deposits lead to reduction in heat and mass transfer. As a result, the temperature of the system rises, cooling equipment is threatened and a total plant shutdown can result. This can be a very costly outcome.

Clearly, efficient cooling water management is critical to the operation of such plants. Cooling water is a major use of water in industry to transfer heat in such systems. If there is inadequate control, the cooling system can present significant difficulty to the plant in several ways, such as loss of production capacity, increased cost of cleaning, increased cost and use of protective chemicals, increased energy use, increased maintenance costs, and reduction in service life of the system and its components.

Industrial Water Treatment (IWT) uses methods to control multiple issues such as: scale inhibition for example $CaCO_3$ and $CaSO_4$; corrosion inhibition of mild steel, copper, brass and other metals; biofouling inhibition; suspended matter inhibition/dispersion for example rust; cleanup/removal of biofilm and scale deposits; together with issues for safety for exposure to the persons doing this work, and disposal of these agents into the environment. Thus there is a need for a simpler, cost effective way to meet these various issues.

Industrial water treatment methods must control corrosion, scale, biofouling, suspended matter deposition, and microbiological activity. These problems are interrelated and one problem cannot be totally isolated from the others. For example, scaling occurs more rapidly in a corroding system; microbiologically induced corrosion is a potentially serious problem in almost all cooling systems; and under-deposit corrosion can lead to rapid failure of otherwise intact metal.

Another area where similar control of corrosion, scale, biofouling, suspended matter deposition, and microbiological activity is desired occurs in oil production, where water is used in the down-hole oil and gas extraction process.

The science and the practice of water treatment is an on-going and evolving effort. Today, more than ever, with populations increasing, the need for the re-use of water becomes important. Specifically, the use of waste water that has been purified enough for re-use in IWT systems is important to conserve water and is a critical consideration to the entire population and environment. Thus any process that can reduce the use of water is beneficial. A more efficient IWT system, without these problems, can be one way to reduce water usage.

Many attempts have been made to address these various IWT needs. There are many suggestions in the literature; however, they have not worked in a commercial, large scale setting. There are treatments for various aspects of these issues being sold and used. Some of this art is discussed below.

Lamb (U.S. Pat. No. 3,291,683) teaches use of alkoxy or alkylthio-substituted alkyl amines and their acid addition salts as biocides.

Walter (U.S. Pat. No. 4,816,061) teaches use of alkylthioalkylamines and their acid addition salts as biocides to control biofouling in cooling towers.

Nalepa (US Patent Appln. 20090178587) teaches 2-(decylthio)ethanamine as a biocide and biofilm dispersant (biodispersant).

Moir (WO 2005/014491) teaches etheramines and their acid addition salts as biocides for control of sulfate-reducing bacteria to prevent $H_2O$ formation and resulting problems including iron sulfide deposits and corrosion present in industrial water systems.

Wolf (U.S. Pat. No. 3,524,719) teaches use of oxyamines and thioamines as steel corrosion inhibitors in sour brines when used in combination with another amine compound such as N,N"-hexachlorobiphenylene)bis(ethylenediamine)

Gartner (U.S. Pat. No. 6,260,561) teaches use of aliphatic amines, including oxyamines, for cleaning swimming pool deposits.

Relenyi (U.S. Pat. Nos. 4,982,004 and 5,025,038) teaches a method of preparation of antimicrobial formulations of thioamine salts but no discussion of their use as scale or corrosion inhibition agents is present. No synergistic effects were described.

Fontana (U.S. Pat. No. 6,183,649) teaches use of thioamine salts as a biofilm remover as part of a multi-component composition to treat water circulating systems for control of white rust (zinc corrosion). No synergistic effects were reported.

2-Hydroxypropane-1,2,3-tricarboxylic acid and other hydroxycarboxylic acids are known in the water treatment industry as chelants, which can dissolve or inhibit inorganic deposits, e.g., calcium and iron salts. This chelant function requires a stoichiometric amount of chelant relative to the inorganic salt [Frayne, C., *Cooling Water Treatment: Principles and Practice*, pub. Chemical Publishing Company, New York, N.Y., pp 145-146 (1999)]. Furthermore, Amjad (U.S. Pat. No. 4,952,327) teaches that 2-hydroxypropane-1, 2,3-tricarboxylic acid is useful to stabilize iron salts in solution and prevent their precipitation; however, it is not a scale inhibitor and is ineffective against carbonate, sulfate, and phosphate salts of calcium. However, it has been reported that 2-hydroxypropane-1,2,3-tricarboxylic acid can act as a "threshold" inhibitor specifically for calcium sulfate scale deposition, which is effective at sub-stoichiometric concentrations (Prisciandaro, M. et al., *Ind. Eng. Chem. Res.* (2003) 42, 6647-6652). Many carboxylic acids are also known as corrosion inhibitors for ferrous metals, but not for copper and copper-based alloys like brass. Mayer teaches the use of certain carboxylic acids as inhibitors of mild steel corrosion at the indicated web site: (http://www.bkgwater.com/clients/bkgwater/upload/fichiers/sound_corrosion_inhibitors_cooling.pdf).

There are some reports of synergisms between certain amines and carboxylic acids for inhibition of carbon steel and copper corrosion, but synergism for scale inhibition or suspended matter dispersion is not known.

Hollander (U.S. Pat. No. 5,128,065) teaches benefits of using chelant compounds such as 2-hydroxypropane-1,2,3-tricarboxylic acid with triazole-type inhibitors for copper corrosion inhibition in highly corrosive brackish waters. Triazoles are heterocyclic amines but do not have properties typical of most amines, for example, they are much less basic than alkyl amines.

Ochoa (*J. Appl. Electrochem.* (2004) 34, 487-493) teaches that mixtures of a certain fatty diamine and a phosphonocarboxylic acid produce a synergistic effect for carbon steel corrosion inhibition. There are no salts taught or made and the compounds were only used for carbon steel corrosion.

Kern (*Electrochimica Acta* (2001) 47, 589-598) teaches an enhanced steel corrosion inhibition by using a basic amine with known carboxylic acid inhibitors, each component contributing to the overall corrosion inhibition. Synergism was not identified or taught.

Amjad (Amjad, Z., presentation AWT-00, Association of Water Technologies, Inc. 12th Annual Convention & Exposition, 2000; also: *Tenside Surf. Det.* (2007) 44, 88-93) teaches that cationic ammonium species, such as quaternary ammonium salts, have negative effects on performance of poly(prop-2-enoic) acid scale and deposit inhibitors.

Thus many attempts have been made to solve these issues for IWT which requires the use of a variety of different agents to provide the desired control for all the issues needed in the water cooling system. The only known agents used to control two of these issues are: (1-hydroxyethan-1,1-diyl)bis(phosphonic acid) used for both scale and corrosion inhibition, and poly(prop-2-enoic) acids used for scale inhibition and suspended matter dispersion.

Clearly, there is still a need for an IWT compound that can perform multiple functions for all these various needs in an industrial cooling water system, which reduces the number of chemicals needed to accomplish all these above purposes, and allows simpler and more cost effective formulations, while reducing exposure of chemicals to persons, animals and the environment in general.

BRIEF SUMMARY OF THE INVENTION

The present invention concerns an ammonium salt compound of Formula (I), which provides multiple uses (i.e., at least two) in an industrial water treatment (IWT) system. It is very unexpected and surprising to find control of more than one problem as discussed above by only one compound of this invention in these IWT systems. However, if desired, two or more compounds of Formula (I) may be used.

Specifically, this invention concerns a method of treating the water in IWT systems, which comprises using, as the active agent, a thioammonium or an oxyammonium salt compound of Formula (I):

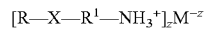

$$[R-X-R^1-NH_3^+]_zM^{-z} \quad \text{Formula (I)}$$

wherein:
R is a straight-chain or branched-chain $C_6$-$C_{24}$ alkyl or a straight-chain or branched-chain $C_6$-$C_{24}$ alkyloxy-$C_2$-$C_3$-alkyl;
X is S or O;
$R^1$ is a straight-chain or branched-chain $C_2$-$C_3$ alkyl;
z is an integer of at least 1 up to the total number of acidic protons on M; and
M is an ionic moiety with a charge greater than or equal to one, is derived from an acid having one or more acidic hydrogens, and has two or more groups capable of coordination to metal cations or electron-deficient sites on a metal surface, selected from the group consisting essentially of the anions derived from: 2-hydroxypropane-1,2,3-tricarboxylic acid; 2,3-dihydroxybutanedioic acid; trihydroxidooxidophosphorus; 1-hydroxyethan-1,1-diyl)bis(phosphonic acid; 2,3,4,5-tetrahydroxyhexanedioic acid; 2,3,4,5,6-pentahydroxyhexanoic acid; hydroxybutanedioic acid; 2-phosphonobutane-1,2,4-tricarboxylic acid; 2,2',2",2'"-(ethane-1,2-diyldinitrilo)tetraacetic acid; nitriloacetic acid; butanetetracarboxylic acid; 2-hydroxyphosphonoacetic acid; polycarboxylic acids, such as poly(prop-2-enoic acid) and poly(Z)-butenedioic acid; polycarboxylic acid copolymers comprising two or more prop-2-enoic acid, (Z)-butenedioic acid, or sulfonated prop-2-enoic acid derivative repeat units; $C_2$-$C_{12}$ dibasic carboxylic acids, including ethanedioic, butanedioic, (Z)-butenedioic, hexanedioic, and nonanedioic acids; and trihydroxidoboron; carboxymethylinulin, and alginic acid; and adding the compound of Formula (I), as a liquid or as a solid or as part of a formulation, to the water of the IWT system in either: a) a continuous or semicontinuous manner for as long as needed to provide the desired control; or b) in a slug dose manner for about 1 day to about 2 months to provide the desired control;

in an effective amount to provide at least two of the following uses: metal corrosion inhibition, scale inhibition, suspended matter dispersion, biocide efficacy, or biofilm removal/biofilm dispersion; and observing or testing the IWT system to confirm such desired control has been obtained.

Such amount of Formula (I) for the desired control has a concentration from about 0.01 to 2000 ppm, preferably from about 1 to about 200 ppm, in the treated water of the IWT system.

In Formula (I), preferred R moieties are those where R is a straight chain or branched chain $C_8$-$C_{14}$ alkyl, more preferably R is a straight chain or branched chain $C_6$-$C_{16}$ alkyl.

In Formula (I) preferred M anions are derived from 2-hydroxypropane-1,2,3-tricarboxylic acid; 2,3-dihydroxybutanedioic acid; trihydroxidooxidophosphorus; 1-hydroxyethan-1,1-diyl)bis(phosphonic acid; 2,3,4,5-tetrahydroxyhexanedioic acid; 2,3,4,5,6-pentahydroxyhexanoic acid; or hydroxybutanedioic acid. More preferred M anions are derived from: 2-hydroxypropane-1,2,3-tricarboxylic acid; 2,3-dihydroxybutanedioic acid; trihydroxidooxidophosphorus; or 1-hydroxyethan-1,1-diyl)bis(phosphonic acid.

In the above method, preferred utilities for compounds of Formula (I) are scale inhibition and suspended matter dispersion.

A subset of the compounds of Formula (I), which are novel, are shown as compounds of Formula (IA) below:

Formula (IA)

wherein:
R is a straight-chain or branched-chain $C_6$-$C_{24}$ alkyl or a straight-chain or branched-chain $C_6$-$C_{24}$ alkyloxy-$C_2$-$C_3$-alkyl;
X is S or O;
$R^1$ is a straight-chain or branched-chain $C_2$-$C_3$ alkyl;
z is a integer of at least 1 such that the compound of Formula (IA) is electrically neutral; and
Q is an ionic moiety with a charge greater than or equal to one, is derived from an acid having one or more acidic hydrogens, and has two or more groups capable of coordination to metal cations or electron-deficient sites on a metal surface, selected from the group consisting essentially of: 2,3-dihydroxybutanedioic acid; 1-hydroxyethan-1,1-diyl)bis(phosphonic acid; 2,3,4,5-tetrahydroxyhexanedioic acid; 2,3,4,5,6-pentahydroxyhexanoic acid; hydroxybutanedioic acid; 2-phosphonobutane-1,2,4-tricarboxylic acid; 2,2',2'',2'''-(ethane-1,2-diyldinitrilo)tetraacetic acid; nitriloacetic acid; butanetetracarboxylic acid; 2-hydroxyphosphonoacetic acid; polycarboxylic acids, such as poly(prop-2-enoic acid) and poly(Z)-butenedioic acid; polycarboxylic acid copolymers comprising two or more prop-2-enoic acid, (Z)-butenedioic acid, or sulfonated prop-2-enoic acid derivative repeat units; $C_2$-$C_{12}$ dibasic carboxylic acids, including butanedioic, (Z)-butenedioic, hexanedioic, and nonanedioic acids; carboxymethylinulin; and alginic acid.

In Formula (IA) preferred Q anions are derived from 2,3-dihydroxybutanedioic acid; 1-hydroxyethan-1,1-diyl)bis(phosphonic acid); 2,3,4,5-tetrahydroxyhexanedioic acid; 2,3,4,5,6-pentahydroxyhexanoic acid; hydroxybutanedioic acid; 2-phosphonobutane-1,2,4-tricarboxylic acid; 2,2',2'',2'''-(ethane-1,2-diyldinitrilo)tetraacetic acid; nitriloacetic acid; butanetetracarboxylic acid; 2-hydroxyphosphonoacetic acid; polycarboxylic acids, such as poly(prop-2-enoic acid) and poly(Z)-butenedioic acid; polycarboxylic acid copolymers comprising two or more prop-2-enoic acid, (Z)-butenedioic acid, or sulfonated prop-2-enoic acid derivative repeat units. The more preferred Q anions are derived from 2,3-dihydroxybutanedioic acid; and 1-hydroxyethan-1,1-diyl)bis(phosphonic acid).

The compounds of Formula (IA) are used in the same manner for the method of treating water in IWT systems as the compounds of Formula (I).

These compounds of Formula (I) provide control for the above discussed needs of an IWT system. Of course, if less than all the functions named above are needed for the issues present in the IWT system, these compounds can still be effective. By having only one compound with multiple uses, the exposure to the persons who use these chemicals is lessened as fewer different chemicals are needed to be added. Also the impact on the environment, for example, chemical waste disposal and re-use of water, is lowered when fewer chemicals are needed.

DETAILED DESCRIPTION OF THE INVENTION

Figure 1:
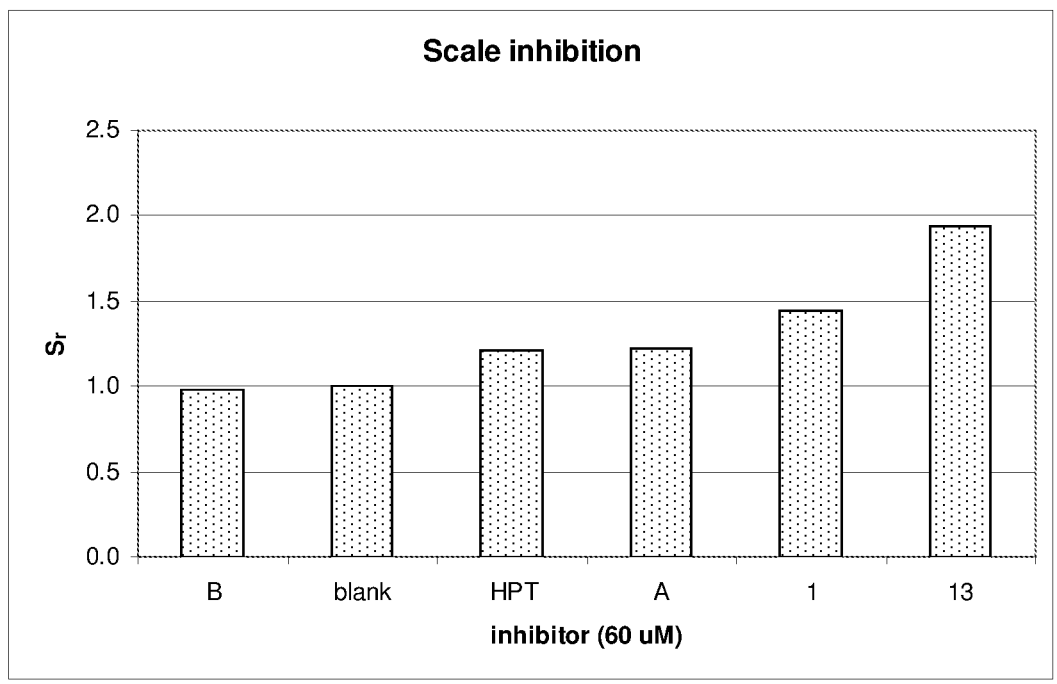
FIG. 1 graphically represents the relative scale inhibition performance of the compounds of Formula (I) and known compounds, where the compounds tested are identified in Table 1 or are known chemicals. In the graph the vertical axis is the supersaturation ratio, $S_r$, and the horizontal axis is the compound tested.
Figure 2:
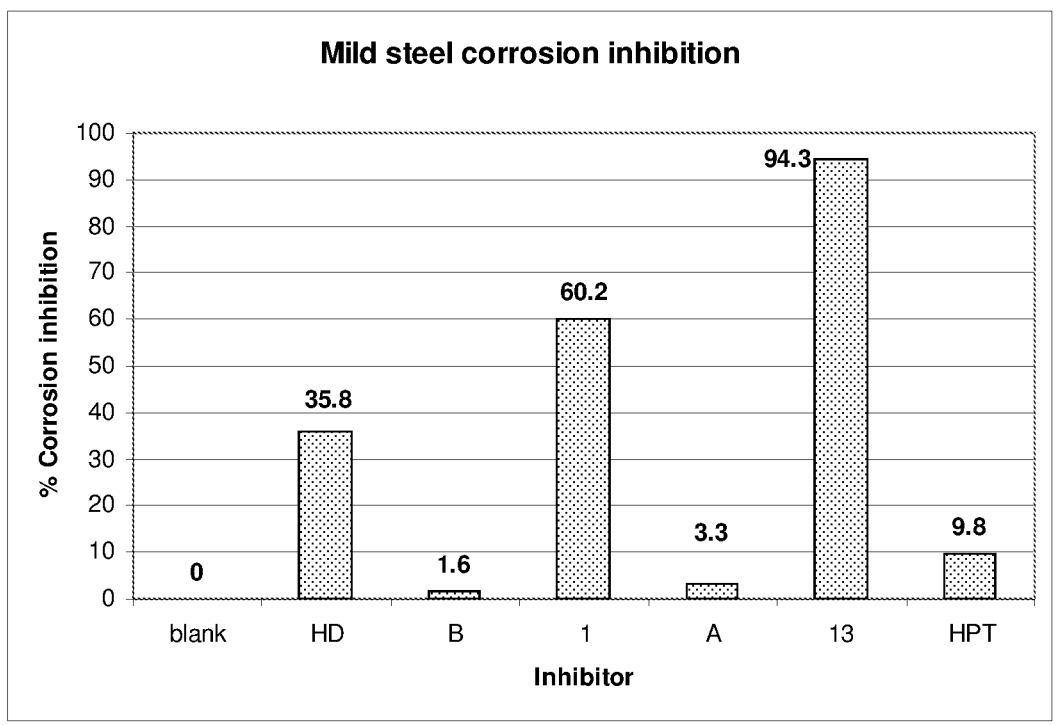
FIG. 2 graphically represents the relative corrosion inhibition of mild steel by the compounds of Formula (I) and known compounds, where the compounds tested are identified in Table 1 or are known chemicals. In the graph the vertical axis is the percent corrosion inhibition, and the horizontal axis is the compound tested.

It is understood that the terminology used herein is for the purpose of describing particular embodiments only and is not intended to be limiting. As used in this specification, the singular forms "a", "an", and "the" include plural referents unless the content clearly indicates otherwise. The following terms in the Glossary as used in this application are to be defined as stated below and for these terms, the singular includes the plural.

Various headings are present to aid the reader, but are not the exclusive location of all aspects of that referenced subject matter and are not to be construed as limiting the location of such discussion.

Also, certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

GLOSSARY

The following terms as used in this application are to be defined as stated below and for these terms, the singular includes the plural.
Biobased means a renewable source such as microbial or yeast fermentation of sugars, or other plant derived material, or from any living material such as plants
COC means cycles of concentration
% means percent by weight unless indicated otherwise
g means grams
h means hour
HD means (1-hydroxyethan-1,1-diyl)bis(phosphonic acid)
HPT means 2-hydroxypropane-1,2,3-tricarboxylic acid
IWT means industrial water treatment and refers, in general, to treatment of water or water-containing fluids which is used to mitigate or control the conditions given in FIG. 9, and encompasses, including but not limited to, cooling towers, closed loop and open loop heat exchangers, plate and frame heat exchangers, chillers, fluid cooled systems, boilers, metal working fluids, oil and gas production well water, crude oil transmission piping, oil storage vessels, gas transmission piping, gas storage vessels, geological formation fracturing operations and fluids, systems which use high efficiency heat transfer tower fill, pipeline cleaning (pigging), reverse osmosis membranes, ultrafiltration membranes, sand filters, and charcoal filters
L means liter
min means minute
mL means milliliter
mpy means mils per year
Na-TAI means the sodium salt of 1,2,3-triaza-1H-indene
Oxyamine (II) means aminopropyloxydecane
RT means room temperature or ambient temperature, about 20-25° C.
sec means second
slug dose means a dose added periodically, usually a large dose added at one time rather than gradually, but may be repeated as necessary
Thioamine (II) means 2-(decylthio)ethanamine

DISCUSSION

As indicated above the issues for IWT are complex and interrelated, for example as shown in http://imexpo.cii.in/presentations/INDUSTRIAL%20COOLING%20WATER-%20MANAGEMENT.pdf. Most IWT systems have multiple issues that need control. These issues are discussed herein to more fully appreciate the difficulty concerned. The following terms are used in the IWT industry as indicated below.
Metal Corrosion
Corrosion basically concerns an electrochemical oxidation process which results in the destruction of the metals that are used in the construction of most cooling towers, e.g., copper, brass, iron, aluminum, and mild steel. Serious weakness in the integrity of the cooling water system can result if left untreated for long times. For example, iron oxide deposits, if not removed, can propagate under-deposit corrosion, restrict water flow, can cause blockages in the system, impede heat transfer, provide a habitat for microbial species and lead to microbiologically influenced corrosion. Thus effective corrosion control usually also includes use of scale inhibitors, biocides and dispersants. Both copper and mild steel are important materials of construction in IWT systems. Copper is preferred for its efficient heat transfer properties in heat exchangers, and mild steel for its cost effective structural properties for use in general structural parts and also in piping.

Additional examples of important corrosion issues in IWT concerns galvanized steel surface corrosion e.g., zinc oxides (white rust) and aluminum corrosion in high pressure boilers and wind power electric generation equipment.
Scale
Deposition of scale in an IWT system is a chemical process that results when the concentration of dissolved salts in the cooling water exceeds their solubility limits and precipitates form on surfaces in contact with the water. The most common scale former is calcium carbonate, a salt which exhibits reverse solubility in that it becomes less soluble as the temperature of the water increases. This property causes calcium carbonate scale formation in the most sensitive area, the heat transfer surfaces of production equipment. Since the thermal conductivity of this scale is substantially less than metal, heat removal is reduced. In extreme cases, enough material precipitates to physically block the cooling water passages, resulting in the affected equipment being removed from operation for either chemical (acid) or mechanical cleaning.

Chemical scale inhibitors function by either:
(A) Selective adsorption on growing scale crystals, thereby converting the crystal structure into a non-scaling type which does not form a hard scale (threshold inhibitors), or
(B) Through chemical reactions with the scale forming ions, converting them into non-scale forming materials (stoichiometric inhibitors, such as chelants).

Threshold inhibitors (Prisciandaro, M. et al., *Ind. Eng. Chem. Res.* (2003) 42, 6647-6652) provide an established method to hinder or delay scale formation and involves the addition of additives in solution. These compounds are added to any given treatment in very small quantities (ppm) so they are called "threshold inhibitors" to describe the mechanism of scale inhibitor at sub-stoichiometric ratios. This threshold effect is explained by an adsorption of the inhibitor onto the crystal growth sites of sub-microscopic crystallite which are initially produced in the supersaturated solution, interfering with crystal growth and altering the morphology of those that grow. This process can prevent crystal growth or at least delay it for prolonged periods of time. Therefore, scale inhibition by a threshold inhibitor is based on kinetic and not thermodynamic effects. A number of investigations have reported that the precipitation of certain calcium salts is significantly reduced in the presence of water soluble additives such as special types of polymers/copolymers with carboxyl groups, organophosphorus compounds, derivatives of phosphonic acid, organic phosphate esters, 2-hydroxypropane-1,2,3-tricarboxylic acid, anionic and cationic surfactants, and some metal ions.

Although sulfur scale is also a problem in IWT systems, it is not a part of this present invention. Sulfur scale is chemically distinguished from calcium carbonate and most other types of scale in that sulfur scale is largely elemental (non-ionic), and formed by a different process in which hydrogen sulfide present in the water is oxidized, either biotically or abiotically, and the resulting sulfur precipitates and forms deposits. Other forms of sulfur-based deposits include iron sulfide, which is a product of reaction of hydrogen sulfide and metallic iron or iron salts. Iron sulfide deposits are controlled by control of hydrogen sulfide formation.

Dispersion of Suspended Matter

Deposition is a general term for all the things that can cause problems in a cooling water system that are NOT due to scale, corrosion, or biological activity. Such deposition can result from scrubbing of airborne material from the ambient air by the cooling tower, process contamination of cooling water by such things as leaking oil coolers, suspended or dissolved corrosion products, and suspended material in the makeup water. Most suspended solids deposition can be controlled by addition of dispersant chemicals like poly(prop-2-enoic acid), poly[(Z)-butenedioic acid], and their copolymers to the cooling water. These materials function by charge neutralization of the suspended particles and then as emulsifying binding agents, breaking up existing deposits and preventing agglomeration of the particles to form new deposits.

Biofouling

Microbiological growth within a cooling water system, if not controlled, can result in formation of biological fouling layers (biofilm) on all surfaces in contact with the cooling water. This biofilm affects process operation much like scale and deposition. Biofilm usually results in a substantial corrosion rate increase due to formation of anaerobic areas under the fouling layer. This creates galvanic couple corrosion and forms metabolic by-products, such as hydrogen sulfide, which can attack the base metals. Control of biological fouling is to periodically dose the cooling system with a biocide and dispersant to kill as many of the organisms present as possible and remove them from the surfaces and into the bulk water where they can be purged from the system.

General Discussion

Figure 9:
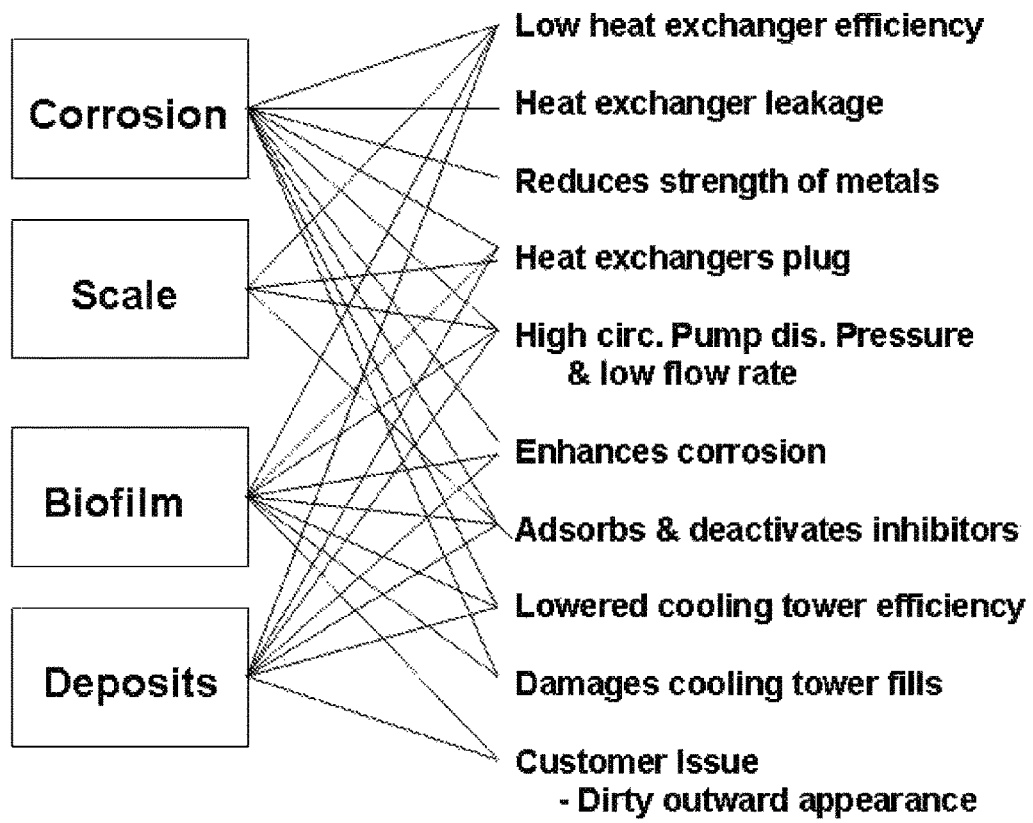
FIG. 9 illustrates the various problems that the present compounds of Formula (I) treats in the present method.

Clearly, previous attempts to control all these various conditions have taken numerous chemicals or mechanical efforts. It is also important to understand which of these conditions is happening and can change over time. FIG. 9 illustrates the interrelationship of these problems such that all must be treated in an IWT system. There presently is no one known commercial treatment with one chemical that can control all these conditions. It is difficult for one compound to provide these various uses because of the diverse requirements for each condition. Cost for IWT use for one compound is expected to be less than multiple chemicals.

Additionally, this invention allows the continued use of water in a cyclical fashion. When used in such a cyclical fashion, the traditional or commonly used chemicals degrade and minerals, salts, other moieties, buildup in those waters. Thus, the water chemical has a 'demand' on it. This invention is resilient to or is not impacted by such buildup nor is it degraded under end-use conditions. Therefore, this invention allows for higher levels of water reuse having increased levels of concentration (COC) of such built up moieties while it lowers demand to add more chemicals. Importantly, this invention allows the use of waste water in the IWT system. Use of waste water is limited because waste water is highly corrosive, toxic, and promotes the buildup of biofilm. This invention has the benefit of allowing the use of waste water, use of the same water over and over again (recycling and/or closed loop system), and prevents biofilm buildup.

Cooling towers, which operate or are designed in the fluid cooled operating mode, are specially benefited by this invention. Oven temperature control in manufacturing processes—such as in the manufacture of carbon fiber used in airplane wing materials—is especially benefited by this invention. In such systems, water from the cooling tower is sprayed onto the tubing that carries the cooling water. The tubing that carries the cooling water is located in the furnaces that provide final heat treatment of the carbon fiber. The tubing is made of copper. The extensive use of such copper tubing is prone to the impact of copper corrosion, formation of biofilm, and deposition of scale. Thus, using the compounds of Formula (I) in the present method provides protection and control of such copper corrosion. The use of individual chemicals to provide such protection is not sufficient to provide the protection in these manufacturing systems. Oxidation is the most critical step in the production of carbon fiber. Since oxidation is an exothermic process, having uniform, consistent airflow to uniformly control heat in the process is required. Consistency of process controls the quality of the carbon fiber and results in no skinning and more uniform densification of the carbon fiber. By using compounds of Formula (I) or (IA) improvements in the carbon fiber process occur by allowing up to 30% faster rates of oxidation and related parameters thereby allowing optimal use of oven designs.

It is very surprising and unexpected to find such a compound that can provide these uses. This invention provides a thioammonium or an oxyammonium salt of Formula (I) or (IA) that has the ability to function for all these uses in an IWT system. These uses include metal corrosion inhibition, scale inhibition, suspended matter dispersion, biocide efficacy, or biofilm removal/biofilm dispersion. The use of one compound of Formula (I) or (IA) for these multiple uses reduces the impact of more chemicals on the environment and exposure to persons handling them. Additionally, these present compounds display greater than additive effects for these multiple uses in IWT systems. The theory of why certain salts provide these multiple uses is still being pursued. Predictability of which salts cause such desired additive effects is not possible. If desired, more than one compound of Formula (I) can be used.

Although some thioamines and oxyamines (as the free amine) and their acid addition salts are known, including to increase their solubility in IWT systems, certain ones are known to be biocides, biofilm dispersants, and copper corrosion inhibitors in industrial water treatment; but these are not known or useful as mild steel corrosion inhibitors, scale inhibitors or suspended matter dispersants. Other compounds which are not amines are known to be effective corrosion inhibitors, scale inhibitors, suspended matter dispersants or dissolvers; but these are not known as biocides or biofilm dispersants. In other ways, various aspects of these present compounds have been used, but not found effective for all uses desired; whereas those compounds of the present invention have more uses. The selection of these compounds of Formula (I) or (IA) as their specified salts was not previously known to be able to control all these various uses needed for industrial water treatment systems.

This invention provides a method of treating the water in IWT systems, which comprises using, as the active agent, a thioammonium or an oxyammonium salt compound of Formula (I):

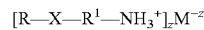   Formula (I)

wherein:

R is a straight-chain or branched-chain $C_6$-$C_{24}$ alkyl or a straight-chain or branched-chain $C_6$-$C_{24}$ alkyloxy-$C_2$-$C_3$-alkyl;

X is S or O;

$R^1$ is a straight-chain or branched-chain $C_2$-$C_3$ alkyl;

z is an integer of at least 1 up to the total number of acidic protons on M; and M is an ionic moiety with a charge greater than or equal to one, is derived from an acid having one or more acidic hydrogens, and has two or more groups capable of coordination to metal cations or electron-deficient sites on a metal surface, selected from the group consisting essentially of the anions derived from: 2-hydroxypropane-1,2,3-tricarboxylic acid; 2,3-dihydroxybutanedioic acid; trihydroxidooxidophosphorus; 1-hydroxyethan-1,1-diyl)bis(phosphonic acid; 2,3,4,5-tetrahydroxyhexanedioic acid; 2,3,4,5,6-pentahydroxyhexanoic acid; hydroxybutanedioic acid; 2-phosphonobutane-1,2,4-tricarboxylic acid; 2,2',2'',2'''-(ethane-1,2-diyldinitrilo)tetraacetic acid; nitriloacetic acid; butanetetracarboxylic acid; 2-hydroxyphosphonoacetic acid; polycarboxylic acids, such as poly(prop-2-enoic acid) and poly(Z)-butenedioic acid; polycarboxylic acid copolymers comprising two or more prop-2-enoic acid, (Z)-butenedioic acid, or sulfonated prop-2-enoic acid derivative repeat units; $C_2$-$C_{12}$ dibasic carboxylic acids, including ethanedioic, butanedioic, (Z)-butenedioic, hexanedioic, and nonanedioic acids; and trihydroxidoboron; carboxymethylinulin, and alginic acid; and adding the compound of Formula (I), as a liquid or as a solid or as part of a formulation, to the water of the IWT system in either: a) a continuous or semicontinuous manner for as long as needed to provide the desired control; or b) in a slug dose manner for about 1 day to about 2 months to provide the desired control;

in an effective amount to provide at least two of the following uses: metal corrosion inhibition, scale inhibition, suspended matter dispersion, biocide efficacy, or biofilm removal/biofilm dispersion; and observing or testing the IWT system to confirm such desired control has been obtained.

Some of the ammonium salts of Formula (I), as used in the present method, are new and have been claimed as a subset of Formula (I) in Formula (IA). The acids for these compound claims are those where Q is: 2,3,4,5-tetrahydroxyhexanedioic, 2,3-dihydroxybutanedioic, hexanedioic, nonanedioic, butanedioic, (Z)-butenedioic, (1-hydroxyethan-1,1-diyl)bis(phosphonic acid), 2-phosphonobutane-1,2,4-tricarboxylic acid, hydroxyphosphonoacetic acid, 2,2',2'',2'''-(ethane-1,2-diyldinitrilo)tetraacetic acid, poly(prop-2-enoic acid), carboxymethylinulin, and alginic acid. Additionally, those compounds of Formula (IA) when X is S and the acid is 2-hydroxypropane-1,2,3-tricarboxylic acid, ethanedioic acid or trihydroxidoboron are new. When X is O in Formula (IA), and the acid is 2-hydroxypropane-1,2,3-tricarboxylic acid, a compound of Formula (IA) is the 2-hydroxypropane-1,2,3-tricarboxylic acid salt of aminopropyloxydecane. Furthermore, when z is greater than 1, then different ratios of the anion to cation are present, e.g. when z is 2, then there is a 1:2 ratio of anion to cation, and these are different compounds with different properties.

The present invention provides a method for metal corrosion inhibition, scale inhibition, suspended matter dispersion, biocide efficacy, or biofilm removal/biofilm dispersion in an industrial water treatment system using a salt of a thioamine or an oxyamine of Formula (I) or (IA).

Preferred amines used to prepare compounds of Formula (I) or (IA) are those where R is a straight chain or branched chain $C_6$-$C_{16}$ alkyl or more preferred $C_8$-$C_{14}$ alkyl. One compound that has been tested is 2-(decylthio)ethanamine hydrochloride (Compound A in the examples). Thioamines are readily produced as described by Berazosky in U.S. Pat. No. 4,086,273. Various salts of this thioamine of Formula (I) or (IA) were also tested. In a similar manner, various derivatives of oxyamines of Formula (I) or (IA) were made and tested. One compound that has been tested is the ethanoic acid salt of aminopropyloxydecane (Compound B in the examples). Oxyamines are produced by known methods such as that of Utermohlen in *J. Am. Chem. Soc.* (1945) 67, 1505-1506.

The composition of the amine salt is important. To have this amine salt of Formula (I) or (IA) suitable for all uses, it is important to consider which acid corresponding to Q or M is combined with the amine to form the salt.

Preferred acids correspond to M anions in Formula (I). These acids alone are commonly used in IWT as separate reagents to provide certain benefits, such as scale or corrosion inhibition. Salts of Formula (I) or (IA) provide an effective mechanism to deliver the benefits of the acids along with the benefits of the amine in one compound. Salts of amines with acids yield more benefits than would be expected from both components alone.

The properties and performance of the salt in IWT also depends on the ratio of each component present. For example, for a dibasic acid such as ethanedioic acid, two salts are possible with an amine, namely, the ammonium hydrogen ethanedioate and the diammonium ethanedioate. Each product is a distinct chemical compound with unique properties. It is not obvious what properties will result in the product by the reaction of ethanedioic acid with an amine of unspecified stoichiometry.

The process to make these salts of Formula (I) or (IA) use one of the following three methods:

The free amine is reacted with the acid either in the absence of solvent or preferably in a solvent (such as water or aqueous 2-propanol) in order to facilitate mixing of the compounds and heat transfer due to the reaction being exothermic. The resulting solution of the salt of Formula (I) or (IA) may be used directly, or evaporated to the desired concentration or completely to its solvent-free form. A solvent-free form may be especially useful if it is a solid which may be formulated in various user-friendly, less waste disposal forms.

Alternatively, a salt of the amine and ethanoic acid is converted to the salt of Formula (I) or (IA) by reacting an acid with the corresponding ammonium ethanoate salt in an aqueous medium. When the pKa of the acid used to make the new ammonium salt is about the same as ethanoic acid or lower, a significant concentration of the new acid salt forms. However, because ethanoic acid is volatile (and the acid is not), the 'free' ethanoic acid evaporates, and by LeChatelier's Principle the equilibrium shifts to form more ethanoic acid. Over time, all of the ethanoic acid evaporates leaving only the new ammonium salt of Formula (I) or (IA). Other acids can be used for the ethanoic acid so long as they are volatile, such as methanoic acid and propanoic acid.

Another method to prepare the compounds of Formula (I) or (IA) involves the reaction of an amine salt with a salt of the desired acid by mixing of the two components in an appropriate solvent.

The amine salts of Formula (I) or (IA) are prepared as described above and then used in an IWT system to control all uses above mentioned. Also these salts can be prepared in situ just prior to use or the components combined (e.g., amine and the acid) upon use at the plant in such a manner that the salt forms.

Although some thioammonium or oxyammonium compounds with different M anion salts than those now listed and claimed (i.e., Cl, ethanoate salt) have been known for various uses, they have not been known for scale inhibition or multiple uses as now claimed. The present compounds of Formula (I) have shown improved utility in these prior uses and can be used for more end applications than the prior compounds. Additionally, surprisingly these present compounds of Formula (I) have shown unexpected synergistic effects (i.e., a non-additive improvement) over the sum of the performance obtained from the corresponding amine and acid compounds alone. These results were very surprising and unexpected as Amjad (Amjad, Z., presentation AWT-00, Association of Water Technologies, Inc. 12th Annual Convention & Exposition, 2000; also: *Tenside Surf. Det.* (2007) 44, 88-93) found that certain cationic nitrogen compounds used in IWT interfere with the performance of anionic water treatment chemicals, such as scale inhibitors and suspended matter dispersants. Thus, the ammonium salt of an anion, such as those stated in Formula (I), would be anticipated to have a reduced effectiveness with respect to the anion's function. It is clearly unpredictable which cations and which anions, even when their respective uses are known, could be combined to obtain an improved and effective use of the resulting compound; certainly not for multiple uses. Thus, this reference is teaching away from the utility of such combinations of ammonium salts and acids of this invention. Clearly, the reference makes predicting what combinations of anion and cations to make compounds to even try for these present uses or which compounds would have such additive effects virtually impossible.

These compounds of Formula (I) or (IA) can be used in conjunction with other known agents in the present method (each as a separate addition or together in a combined formulation) when conditions exist that such additional agent(s) are desirable. Use of a combination of water treatment chemicals, for example, scale inhibitors, corrosion inhibitors, suspended matter dispersants, biocides, biofilm removal agents, and biofilm dispersants, is a common practice. The combination of additional active ingredients does not alter the effect of the compounds of Formula (I) or (IA) used in this method.

Additionally, the compounds of Formula (I) or (IA) can be used in conjunction with other known inert ingredients in the present method (each as a separate addition or together in a combined formulation) when conditions exist that such inert ingredients(s) are desirable. Such inert ingredients are water, solvents, diluents, excipients, stabilizers, surfactants, and antifoaming agent.

These compounds of Formula (I) or (IA) may be used alone in the present method for less than all uses stated in the present method when desired.

In the present method, IWT is used to treat water-containing fluids to mitigate or control the conditions given in FIG. 9. These IWT systems encompass, but are not limited to, cooling towers, closed loop and open loop heat exchangers, plate and frame heat exchangers, chillers, fluid cooled systems, boilers, metal working fluids, oil and gas production well water, crude oil transmission piping, oil storage vessels, gas transmission piping, gas storage vessels, geothermal storage fluids, geological formation fracturing operations and fluids, systems which use high efficiency heat transfer tower fill, pipeline cleaning (pigging), reverse osmosis membranes, ultrafiltration membranes, sand filters, charcoal filters, water in toilets, portable toilets, urinals, spas, mineral baths, and swimming pools.

A compound of Formula (I) or (IA) is used in the form of a liquid or solid. Also it can be diluted in a solution. The solids can be, for example, a powder, tablet, block, pellet, or granule, or formulated for controlled release. The liquid includes solutions, emulsions, suspensions, solvent-free liquid, gels, or dispersions. Also the other active agents and inert ingredients can be present when desired. The present method introduces the compound of Formula (I) or (IA) in a continuous manner, semicontinuous manner, or as a slug dose into the IWT system. The liquids may be introduced into the IWT system by a chemical metering pump or simply pouring from a container such as a pail into the water to be treated. The solids may be introduced directly into the IWT systems as one mass which gradually dissolves or with the aid of solid feeder devices in which the solid is dissolved or suspended in water and then introduced at a controlled rate. The controlled or slow release may be obtained by using a semipermeable membrane or appropriate solid formulation.

The amount of compound of Formula (I) or (IA) that is used in such IWT system is in an amount sufficient to provide the control desired, such amount has a concentration of from 0.01 to 2000 ppm, preferably from about 1 to about 200 ppm, in the treated water.

In certain applications such as oil production, the compound of Formula (I) or (IA) may be forced into the geological formation under high pressure (squeeze treatment method). In other applications, it may also be adsorbed onto an inert substrate and then used to treat the water, such as in a sand filter.

The invention will be further clarified by a consideration of the following examples, which are intended to be purely exemplary of the present invention.

The letter examples are directed to the preparation of starting materials and used as comparative examples. The numbered examples are directed to the compounds of the present invention of Formula (I) and (IA).

The amines used were made as described above.

The acids were purchased from various sources which are shown in parentheses, and used as received: 2-hydroxypropane-1,2,3-tricarboxylic acid monohydrate (Mallinckrodt Baker), 2-hydroxypropane-1,2,3-tricarboxylic acid, anhydrous (Southeastern Laboratories), (Z)-butenedioic acid (Fisher), butanedioic acid (Fisher), ethanedioic acid dihydrate (J. T. Baker), nonanedioic acid (Sigma-Aldrich), 2,3-dihydroxybutanedioic acid (Fisher), trihydroxidoboron (Columbia Chemical Industries), trihydroxidooxidophosphorus (85%, Fisher), (1-hydroxyethan-1,1-diyl)bis(phosphonic acid) (Belclene™ 660, 60% solution in water, from BWA), poly(prop-2-enoic acid) (Acusol™ 445ND, sodium salt, average molecular weight 4500, The Dow Chemical Company), and 2,3,4,5-tetrahydroxyhexanedioic acid, monopotassium salt (Sigma-Aldrich).

Preparation of Compounds of Formula (I) and Comparatives

Example A and Comparative Example A: Preparation of Thioammonium (II) Chloride

Thioammonium chloride was isolated from a liquid 15% formulation by crystallization. A sample of this solution was placed in a round-bottom flask and reduced to half of its original volume on a rotary evaporator (water aspirator vacuum of approximately 10 Torr and a 50° C. water bath). Acetonitrile (approximately equal in volume to the volume of concentrated Thioammonium (II) chloride in the flask) was added to the clear, dark orange/brown liquid. The milky solution, containing some precipitate after the addition, was refrigerated at approximately 40° F. overnight during which time the solution solidified. The solid was broken up and the mixture filtered in vacuo. After washing with additional acetonitrile, the pale brown/cream-colored crystalline Thioammonium (II) chloride was air dried. Percent recovery of Thioammonium (II) chloride was 50-60%.

Example 1: Preparation of the Salt of Thioamine (II) and 2-Hydroxypropane-1,2,3-tricarboxylic Acid (1:1 Molar Stoichiometry)

A clear, slightly viscous solution of Thioammonium (II) chloride (13.84 g), prepared by the procedure of Example A, in distilled water (200 mL) was prepared in a 1 L separatory funnel. In another container, 4.8 g of commercial 50% NaOH solution was diluted to a volume of 10 mL with distilled water. While manually swirling the separatory funnel, the aqueous NaOH solution was added over about 30 sec. Two layers formed: a yellow top layer and a cloudy milk-white bottom layer. The bottom layer was separated and discarded. To the yellow layer remaining in the separatory funnel was added 2-propanol (3×10 mL) resulting in separation of more water which was separated and discarded. The remaining solution was then added directly to a solution of 2-hydroxypropane-1,2,3-tricarboxylic acid monohydrate (12.6 g) in distilled water (30 mL) and diluted to 100.0 g. The yield was 84% based on Thioamine (II) content. This aqueous solution of the salt of Thioamine (II) and 2-hydroxypropane-1,2,3-tricarboxylic acid was used directly in subsequent testing.

Example 2: General Preparation of Oxyammonium Salts (Method 1)

A: Preparation of the Salt of Oxyamine (II) and (Z)-Butenedioic Acid (1:1 Molar Stoichiometry)

(Z)-Butenedioic acid (11.6 g) was dissolved in distilled water (60 mL). To this stirred solution was added, quickly in one portion, a solution of Oxyamine (II) as its free amine (21.5 g) dissolved in 2-propanol (40 mL). The empty flask was rinsed with 2-propanol (10 mL) and the liquid was poured into the reaction vessel. The mixing was slightly exothermic (10-15° C. rise in solution temperature) and produced a clear, light green/yellow solution. The solution was transferred to an evaporating dish and the dish was left in the hood to evaporate volatiles at RT. As the volatiles evaporated, the solution became a darker yellow, slightly orange-tinted color with a viscous layer floating over the solution. When the material appeared to be dry, the evaporating dish was placed in a vacuum desiccator (3-8 Torr) for several hours to complete the drying process. The product was obtained as a light orangish-white waxy paste (28.0 g, 85% yield).

B: In a similar manner to the process in Example 2A, the amine was reacted with the corresponding acid to provide a salt as named below:
  Salt of Oxyamine (II) and Butanedioic acid salt (1:1 molar stoichiometry), yield 98%,
  Salt of Oxyamine (II) and Nonanedioic acid salt (1:1 molar stoichiometry), yield 99%
  Salt of Oxyamine (II) and Ethanedioic acid salt (1:1 molar stoichiometry, yield 88%
  Salt of Oxyamine (II) and 2,3-Dihydroxybutanedioic acid salt (1:1 molar stoichiometry), yield 84%
  Salt of Oxyamine (II) and Trihydroxidooxidophosphorus salt (1:1 molar stoichiometry), yield 80%
  Salt of Oxyamine (II) and 2,3,4,5-Tetrahydroxyhexanedioic acid salt (1:1 molar stoichiometry), yield 98%

Example B and Comparative Example B: Preparation of a Salt of Oxyamine (II) and Ethanoic Acid In a similar manner to the process in Example 2A, a salt of Oxyamine (II) and ethanoic acid was prepared, yield 85%.

Example 3: General Preparation of Oxyammonium Salts (Method 2)

A: Preparation of a Salt of Oxyamine (II) and (1-Hydroxyethan-1,1-diyl)bis(phosphonic acid) (1:1 Molar Stoichiometry)

(1-Hydroxyethan-1,1-diyl)bis(phosphonic acid) solution (3.43 g solution) was diluted to a volume of 5 mL with distilled water. In one portion, this solution was poured into a solution of a salt of Oxyamine (II) and ethanoic acid (2.75 g; prepared by the procedure Example B) in 2-propanol (10 mL). The reaction mixture was placed in an evaporating dish in a hood and allowed to evaporate at RT. As the volatiles evaporated, the solution became a viscous, pale yellow gel. When the material appeared to be dry, it was placed in a vacuum desiccator (3-8 Torr) for several hours to complete the drying process. The product (3.39 g, 80%) was obtained as a white solid.

B: In a similar manner to the process in Example 3A, a salt of Oxyamine (II) and ethanoic acid was reacted with the corresponding acid to provide:
  Salt of Oxyamine (II) and (1-Hydroxyethan-1,1-diyl)bis(phosphonic acid) salt (2:1 molar stoichiometry), yield 85%
  Salt of Oxyamine (II) and Poly(prop-2-enoic acid) salt (1:1 and 0.2:1 stoichiometries), yield 65 and 84%, respectively
  Salt of Oxyamine (II) and 2-Hydroxypropane-1,2,3-tricarboxylic acid salt (1:1 molar stoichiometry), yield 106% (residual solvent present)

Example 4: Preparation of Salt of Oxyamine (II) and Trihydroxidoboron (1:3 Molar Stoichiometry)

The preparation of Vineyard, B. D. et al. in *Inorg. Chem.* (1964) 3(8), 1144-1147 was followed.

Oxyamine (II) (12.21 g), trihydroxidoboron (3.53 g), and water (3.6 mL) were added to toluene (50 mL) in a round bottom flask fitted with a Dean-Stark water trap and condenser. The mixture was stirred at about 45° C. for 30 min, and then the mixture was heated to reflux for 1 h. The water that collected in the trap was cloudy and the toluene/water interface was not clearly visible. Acetonitrile (25 mL) was added and reflux was continued for an additional 15 min Upon cooling, the reaction flask contained a gelatinous slightly greenish-white translucent precipitate. This material was collected by filtration and placed in a vacuum desiccator (3-8 Torr) for several days. The product was obtained as a white, free-flowing solid (14.4 g, 77.4% yield). The product formed is thought to be in part:

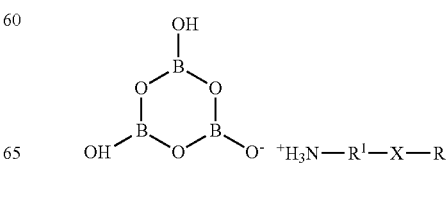

Example 5

Various Salts of Formula (I) are provided in the following Table 1 below.

$S_r$) is shown in Table 2. These compounds were tested at 60 µM concentration except where noted otherwise. Compound numbers are from Table 1.

TABLE 1

| Sample No. | Cation in Formula (I) | Anion derived from the following acid | Prepared by Example No. | Stoichiometry Cation:Anion | Physical Characteristics | % Yield |
|---|---|---|---|---|---|---|
| A | Thioammonium (II) | HCl | A | 1:1 | Free flowing solid | n/a |
| 13 | Thioammonium (II) | 2-Hydroxypropane-1,2,3-tricarboxylic acid | 1 | 1:1 | White waxy solid | 84 |
| B | Oxyammonium (II) | Ethanoic acid | B | 1:1 | Liquid | 85 |
| 1 | Oxyammonium (II) | 2-Hydroxypropane-1,2,3-tricarboxylic acid | 3 | 1:1 | Orange syrup | 106 |
| 2 | Oxyammonium (II) | Ethanedioic acid | 2 | 1:1 | Waxy, free flowing solid | 88 |
| 3 | Oxyammonium (II) | Trihydroxidooxidophosphorus | 2 | 1:1 | Sticky white semisolid | 80 |
| 4 | Oxyammonium (II) | (1-Hydroxyethan-1,1-diyl)bis(phosphonic acid) | 3 | 1:1 | White solid | 80 |
| 5 | Oxyammonium (II) | (1-Hydroxyethan-1,1-diyl)bis(phosphonic acid) | 3 | 2:1 | White solid | 85 |
| 6 | Oxyammonium (II) | Poly(prop-2-enoic acid) | 3 | 1:1 | White solid | 65 |
| 7 | Oxyammonium (II) | Poly(prop-2-enoic acid) | 3 | 0.2:1* | White solid | 84 |
| 8 | Oxyammonium (II) | 2,3-Dihydroxybutanedioic acid | 2 | 1:1 | White solid | 84 |
| 9 | Oxyammonium (II) | (Z)-Butenedioic acid | 2 | 1:1 | Orange white paste | 85 |
| 10 | Oxyammonium (II) | Butanedioic acid | 2 | 1:1 | Pale yellow-white sticky solid | 98 |
| 11 | Oxyammonium (II) | Nonanedioic acid | 2 | 1:1 | Light yellow syrup | 99 |
| 12 | Oxyammonium (II) | Trihydroxidoboron | 4 | 1:3 | White solid | 77 |
| 14 | Oxyammonium (II) | 2,3,4,5-tetrahydroxyhexanedioic acid | 5 | 1:1 | Green-yellow paste | 98 |

*remainder of cation content (0.8 equivalents) is sodium

Methods of Use of Compounds of Formula (I)

The following examples illustrate the uses of the salts of Formula (I) listed in Table 1. Surprisingly, several of these salts of Formula (I) have the ability to provide multiple uses in one compound upon selection of the desired anion, whereas salts comprising other anions are not as effective for multiple uses, as shown below.

Scale Inhibition

The following general procedure was used to measure the calcium carbonate scale inhibition of various compounds of Formula (I) and generally followed the method of Drela, I. et al., *Wat. Res.* (1998) 32, 3188-3191.

To a 100 mL beaker were added 60 mL of HPLC-grade water and 3 mL of 0.1 M calcium chloride. An appropriate amount (0.5-4 mL) of an aqueous solution of the inhibitor compound of Formula (I) to be tested was then added. The solution was magnetically stirred at a constant speed for all experiments. The sample was then titrated with 0.1 M sodium carbonate. After addition of each 0.2 mL aliquot of sodium carbonate titrant, the solution was mixed for 1 min and then the conductivity of the solution measured.

As titrant is added the conductivity increases in a linear fashion. When the supersaturation point is reached, the conductivity decreases and precipitation begins. This is considered the endpoint of the titration. The resulting titration endpoint volumes are used to calculate a relative supersaturation ratio ($S_r$). This is the ratio of the supersaturation of calcium carbonate in the presence of the compound of Formula (I) being tested to the value of the supersaturation of water without inhibitor (distilled water plus 3 mL of 0.1 M calcium chloride). Thus, compounds with $S_r>1$ are displaying scale inhibition.

The scale inhibition performance of various compounds of Formula (I) and comparative compounds were compared at the same molar concentration. The relative calcium carbonate scale inhibition performance (supersaturation ratio,

TABLE 2

| Compound | Conc µM | $S_r$ |
|---|---|---|
| Blank | — | 1.0 |
| 2-hydroxypropane-1,2,3-tricarboxylic acid | 63 | 1.2 |
| A | 64 | 1.2 |
| B | 60 | 1.0 |
| 1 | 60 | 1.4 |
| 13 | 61 | 1.9 |
| 13 | 120 | 2.5 |
| 13 | 180 | 2.8 |
| 2-phosphonobutane-1,2,4-tricarboxylic acid | 5.9 | 3.0 |
| (1-hydroxyethan-1,1-diyl)bis(phosphonic acid) | 45 | 2.5 |
| 8 | 60 | 1.3 |
| 8 | 120 | 1.5 |
| 2,3-Dihydroxybutanedioic acid | 60 | 1.0 |
| 4 | 60 | 4.3 |
| (1-hydroxyethan-1,1-diyl)bis(phosphonic acid) | 60 | 4.4 |
| Butanedioic acid | 60 | 1.0 |
| 10 | 60 | 1.0 |
| 2,3,4,5-tetrahydroxyhexanedioic acid | 60 | 1.4 |
| 14 | 60 | 1.3 |

Some of this data is shown graphically in FIG. 1.

Compound B showed no scale inhibition at this concentration. Compound A and 2-hydroxypropane-1,2,3-tricarboxylic acid showed similar but small amounts of scale inhibition. Compound 13 showed better scale inhibition than Compound 1 but both were scale inhibitors. However Compound 13 was not as effective as the standard scale inhibitor 2-phosphonobutane-1,2,4-tricarboxylic acid at the same 60 µM concentration; but Compound 13 at 180 µM gave similar results as 2-phosphonobutane-1,2,4-tricarboxylic acid at 60 µM. Compound 13 at 120 µM was similar to (1-hydroxyethan-1,1-diyl)bis(phosphonic acid) at 45 µM.

Compound 13, the salt of Thioamine (II) and 2-hydroxypropane-1,2,3-tricarboxylic acid salt, ($S_r$=1.9) was more effective than expected. The additive effects of Compound A, Thioammonium (II) chloride (1.2) plus 2-hydroxypropane-1,2,3-tricarboxylic acid (1.2) on a 1:1 molar basis which would be expected to provide $S_r=1.4$. Compound 1, the salt of Oxyamine (II) and 2-hydroxypropane-1,2,3-tricarboxylic acid, ($S_r=1.4$) was more effective than expected from the additive effects of Compound A (1.0; no effect) plus 2-hydroxypropane-1,2,3-tricarboxylic acid (1.2) on a 1:1 molar basis which would be 1.2.

2-Hydroxypropane-1,2,3-tricarboxylic acid is not reported to be a $CaCO_3$ scale inhibitor. Neither Compound A nor B is known to be a $CaCO_3$ scale inhibitor. Thus it is surprising that the 2-hydroxypropane-1,2,3-tricarboxylate salt of these compounds possessed a significant scale inhibition and especially that it enabled a greater than additive increase in scale inhibition compared to its amine and 2-hydroxypropane-1,2,3-tricarboxylic acid components. Although the respective amines were not tested because of their poor water solubility, the tested hydrochloride (Compound A) or ethanoic acid salt (Compound B) is expected to give equivalent results to their respective free amines because the chloride and ethanoate anions are not known to have significant effects on scale inhibition at these low concentrations.

Additionally, in the above mentioned Drela reference, when the concentration of a scale inhibitor is doubled, it was reported to yield a less-than-additive $S_r$ result (i.e., less than double). Their result is also confirmed by the data for Compound 13 when the concentration is increased from 60 to 120 to 180 µM. Thus, when two inhibitors are combined at the same concentration, less than additive results are actually expected. Clearly, these present data observed greater than additive results with Compound 1 and Compound 13; these results were not expected and very surprising.

In addition to the unexpected benefits observed for Compounds 13 and 1, the 2-hydroxypropane-1,2,3-tricarboxylate salt of Thioamine (II) and Oxyamine (II), respectively, Compound 8, the salt of 2,3-dihydroxybutanedioic acid and Oxyamine (II), ($S_r=1.3$) also was more effective than expected from the additive effects of Compound A (1.0; no effect) plus 2,3-dihydroxybutanedioic acid (1.0) on a 1:1 molar basis, which would be 1.0. Thus the unexpected improvements for the 2-hydroxypropane-1,2,3-tricarboxylic acid salts of Oxyamine (II) is also seen with the structurally similar salt of 2,3-dihydroxybutanedioic acid.

Thus the thioammonium and oxyammonium salts of an acid of Formula (I) and (IA) possess good calcium carbonate scale inhibition and in addition show an unexpected, greater than additive increase in scale inhibition when contrasted to either the thioamine and oxyamine as their chloride or ethanoate salts, respectively, or the dibasic acids, individually.

Corrosion Inhibition

Corrosion inhibition studies of various compounds of Formula (I) were conducted according to ASTM method G31-72 (2004). The following is the general test method.

Aqueous solutions of the test compound (900 mL) were prepared with city water for mild steel corrosion studies or a dilute sea salt solution (1000 ppm in deionized water) for copper corrosion studies. The solutions were magnetically stirred at a constant rate in a 1 L beaker and three coupons of either mild steel or copper were suspended in each beaker. After 5 days (steel) or 7 days (copper), the coupons were removed and cleaned according to ASTM method G1-03. Average weight loss was determined for each set of three coupons and then converted to corrosion rate in terms of mils per year (mpy).

A. Mild Steel

These tests compare the corrosion inhibition of compounds of Formula (I), namely from Table 1, in the first set of comparisons, Compound A with Compound 13, and Compound B with Compound 1, and with 2-hydroxypropane-1,2,3-tricarboxylic acid. Thus five samples were tested relative to a blank and a standard, (1-hydroxyethan-1,1-diyl)bis(phosphonic acid), after 5 days at 26 µM concentrations. The results are shown in Table 3 in terms of corrosion rate (mpy) and relative corrosion inhibition, expressed by the following formula:

% inhibition=[corrosion rate (inhibitor)−corrosion rate (blank)]/corrosion rate (blank)×100%

Table 3 below shows the relative corrosion rate. Concentrations were 26 µM.

TABLE 3

| Solution | Corrosion rate (mpy) | Inhibition relative to blank (%) |
| --- | --- | --- |
| Blank | 25 | 0 |
| (1-Hydroxyethan-1,1-diyl)bis(phosphonic acid) | 16 | 36 |
| Compound B | 24 | 2 |
| Compound 1 | 10 | 60 |
| Compound A | 24 | 3 |
| Compound 13 | 1 | 94 |
| 2-Hydroxypropane-1,2,3-tricarboxylic acid | 22 | 10 |

Under these testing conditions for Table 3 with mild steel coupons and at this inhibitor concentration these results show that Compounds 1 and 13 demonstrate a greater than additive corrosion inhibition compared with Compound B and Compound A, respectively, and with 2-hydroxypropane-1,2,3-tricarboxylic acid alone. The comparative Compounds B (1.6%) and A (3.3%) do not show a significant corrosion inhibition. 2-Hydroxypropane-1,2,3-tricarboxylic acid is a known mild steel corrosion inhibitor and shows a small amount of inhibition (9.8%). Compounds 1 (60%) and 13 (94%) of Formula (I) showed a dramatic improvement in corrosion inhibition over 2-hydroxypropane-1,2,3-tricarboxylic acid and their respective comparative compounds. These results were greater than the sum of the 2-hydroxypropane-1,2,3-tricarboxylic acid and their comparative compound. Thus there is an unexpected, greater than additive improvement in corrosion inhibition from use of the compounds of Formula (I). Also both Compound 1 and 13 have a greater corrosion inhibition on a molar concentration basis than (1-hydroxyethan-1,1-diyl)bis(phosphonic acid), a known mild steel corrosion inhibitor commonly used in industrial water treatment. Although the respective amines were not tested because of their poor water solubility, the tested hydrochloride (Compound A) or ethanoic acid salt (Compound B) is expected to give equivalent results to their respective free amines because the chloride and ethanoate anions are not known to have significant effects on corrosion inhibition at these low concentrations.

Additional mild steel corrosion tests were performed at 130 µM concentration of compounds of Formula (I) and comparative compounds for 5 days. The next test compared the corrosion inhibition of Compound 8 with 2,3-dihydroxybutanedioic acid and Compound B, and Compound 4 with (1-hydroxyethan-1,1-diyl)bis(phosphonic acid) and Compound B. Also included was Compound 1 for reference. The results are shown in Table 4. Concentrations in this set were 130 µM.

TABLE 4

| Solution | Corrosion rate (mpy) | Inhibition relative to blank (%) |
|---|---|---|
| Blank | 24 | 0 |
| 2,3-Dihydroxybutanedioic acid | 20 | 20 |
| Compound 8 | 14 | 44 |
| (1-Hydroxyethan-1,1-diyl)bis(phosphonic acid) | 9.3 | 62 |
| Compound 4 | 7.7 | 68 |
| Compound B | 25 | −1 |
| Compound 1 | 2.9 | 88 |

Note that non-additive improvements were observed for both Compound 8 and Compound 4 relative to their components. Compound 8 (44% inhibition) was greater than the sum of 2,3-dihydroxybutanedioic acid (20%) and Compound B (−1%). Compound 4 (68% inhibition) is greater than the sum of (1-hydroxyethan-1,1-diyl)bis(phosphonic acid) (62%) and Compound B (−1%). Concentrations in this set were 130 µM.

TABLE 5

| Solution | Corrosion rate (mpy) | Inhibition relative to blank (%) |
|---|---|---|
| blank | 12.5 | 0 |
| Compound B | 12.7 | −1 |
| Trihydroxidooxidophosphorus | 7.4 | 40 |
| Compound 3 | 5.6 | 55 |
| Ethanedioic acid | 14.5 | −16 |
| Compound 2 | 15.2 | −21 |
| Compound 1 | 1.6 | 87 |

Note a non-additive improvement was observed for Compound 3, but not for Compound 2 relative to their components. Compound 3 (55% inhibition) was greater than the sum of trihydroxidooxidophosphorus (40%) and Compound B (−1%). Compound 2 and ethanedioic acid were both slightly corrosive relative to the blank.

B. Copper

The first test of copper corrosion inhibition compared Compound A with Compound 13 (from Table 1), 2-hydroxypropane-1,2,3-tricarboxylic acid, and a commercial inhibitor, Na-TAI. These results in Table 6 show the corrosion inhibition performance of 4 inhibitors relative to a blank after 7 days at equimolar concentrations (17 µM).

TABLE 6

| Solution | Compound | Corrosion rate (mpy) | Inhibition relative to blank (%) |
|---|---|---|---|
| 1 | None | 1.7 | 0 |
| 2 | Na-TAI | 0.5 | 71 |
| 3 | Compound A | 1.0 | 41 |
| 4 | Compound 13 | 0.7 | 59 |
| 5 | 2-hydroxypropane-1,2,3-tricarboxylic acid | 1.7 | 0 |

Figure 3:
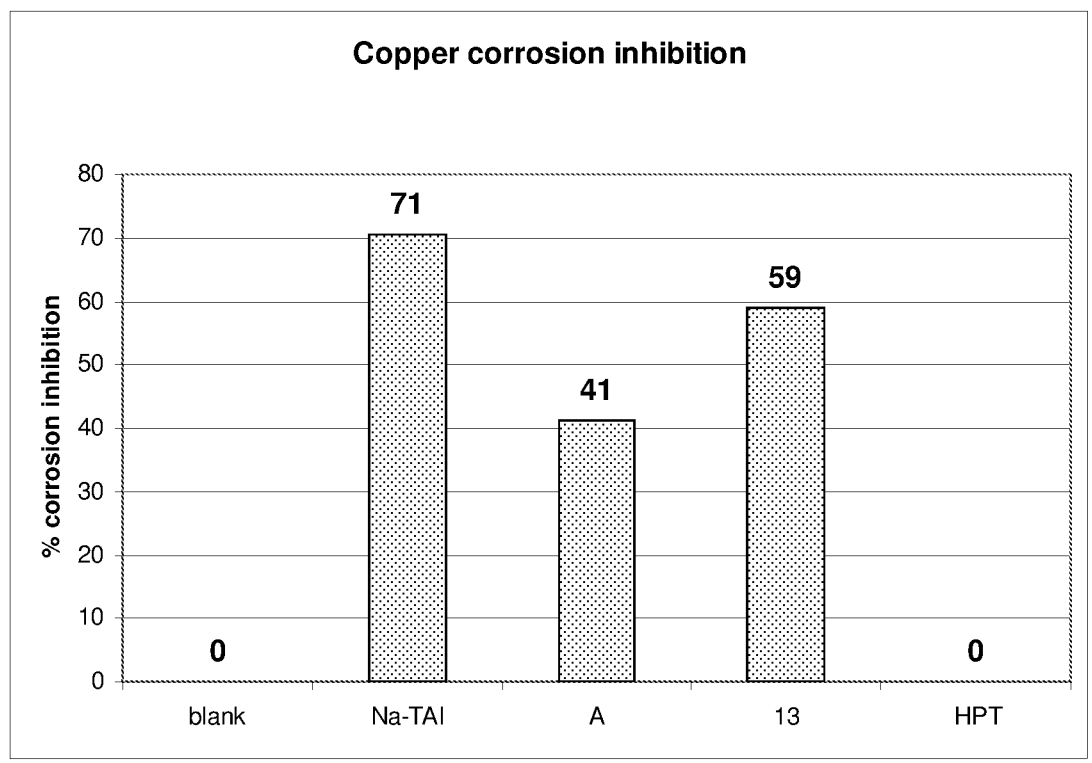
FIG. 3 graphically represents the relative corrosion inhibition of copper by a compound of Formula (I) and known compounds, where the compounds tested are identified in Table 1 or are known chemicals. In the graph the vertical axis is the percent corrosion inhibition, and the horizontal axis is each of the compounds tested.

These data are shown graphically in FIG. 3 in terms of % inhibition.

As shown in Table 6, under these testing conditions with copper coupons and at this inhibitor concentration Compound A (41%) showed significant corrosion inhibition. 2-hydroxypropane-1,2,3-tricarboxylic acid (0%) did not show significant amounts of inhibition. Compound 13 (59%) showed a high level of inhibition, and significantly more inhibition then Compound A or 2-hydroxypropane-1,2,3-tricarboxylic acid. Also Compound 13 showed greater than an additive effect than the sum of Compound A and 2-hydroxypropane-1,2,3-tricarboxylic acid. Compound 13 has a similar corrosion inhibition on a molar basis as Na-TAI, a copper corrosion inhibitor commonly used in industrial water treatment. This result is an unexpected, surprising improvement for Compound 13 of Formula (I). Concentrations in this set were 42 µM.

TABLE 7

| Solution | Compound | Corrosion rate (mpy) | Inhibition relative to blank (%) |
|---|---|---|---|
| 1 | None | 1.5 | 0 |
| 2 | Compound B | 1.0 | 32 |
| 3 | Compound 1 | 0.70 | 54 |
| 4 | 2-hydroxypropane-1,2,3-tricarboxylic acid | 1.4 | 9 |

Figure 4:
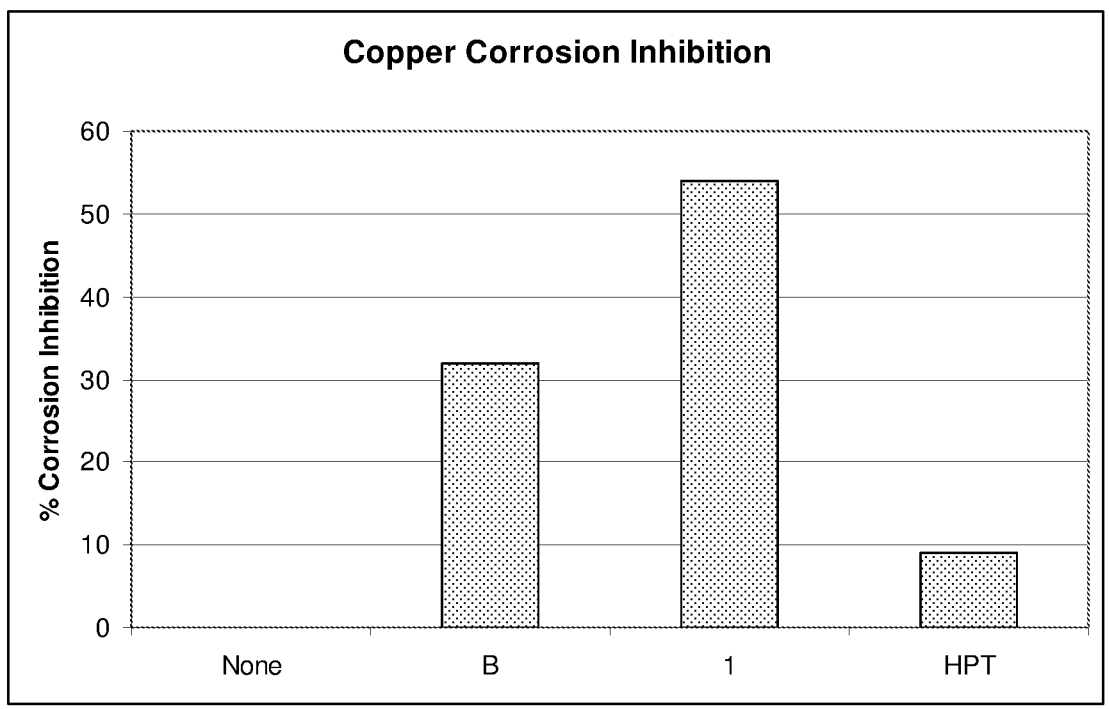
FIG. 4 graphically represents the relative corrosion inhibition of copper by an additional compound of Formula (I) and known compounds, where the compounds tested are identified in Table 1 or are known chemicals. In the graph the vertical axis is the percent corrosion inhibition, and the horizontal axis is each of the compounds tested.
Figure 5:
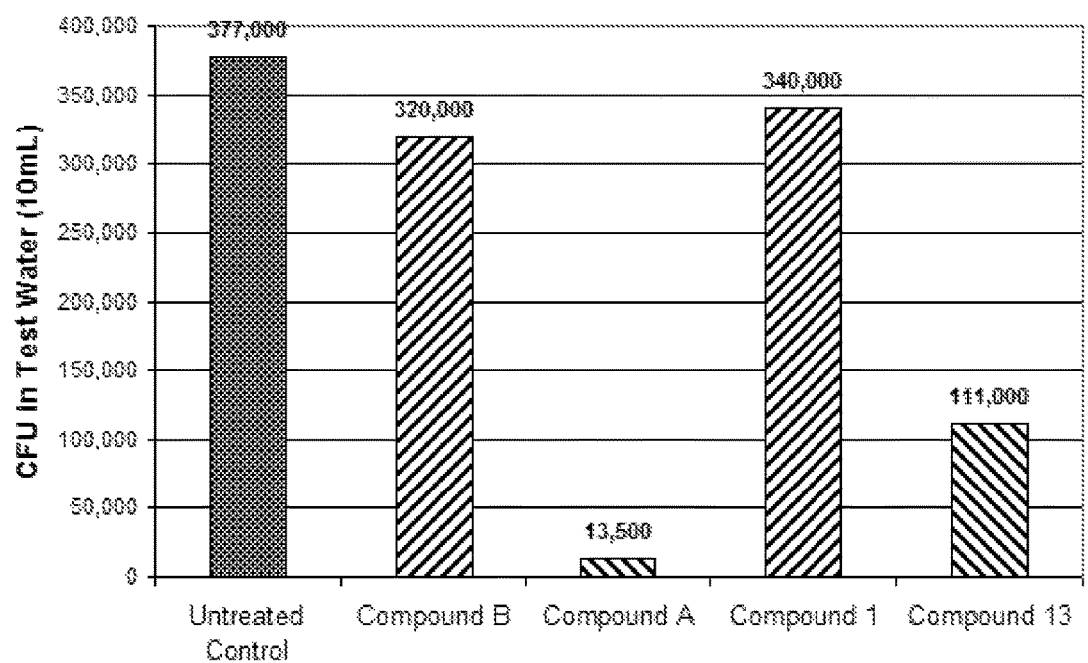
FIG. 5 graphically represents the biocide efficacy after 54 hours incubation against planktonic organisms for the compounds of Formula (I), where the compounds tested are identified in Table 1. In the graph the vertical axis is the microbial population measured as CFU in 10 mL of test water, and the horizontal axis is the compound tested.
Figure 6:
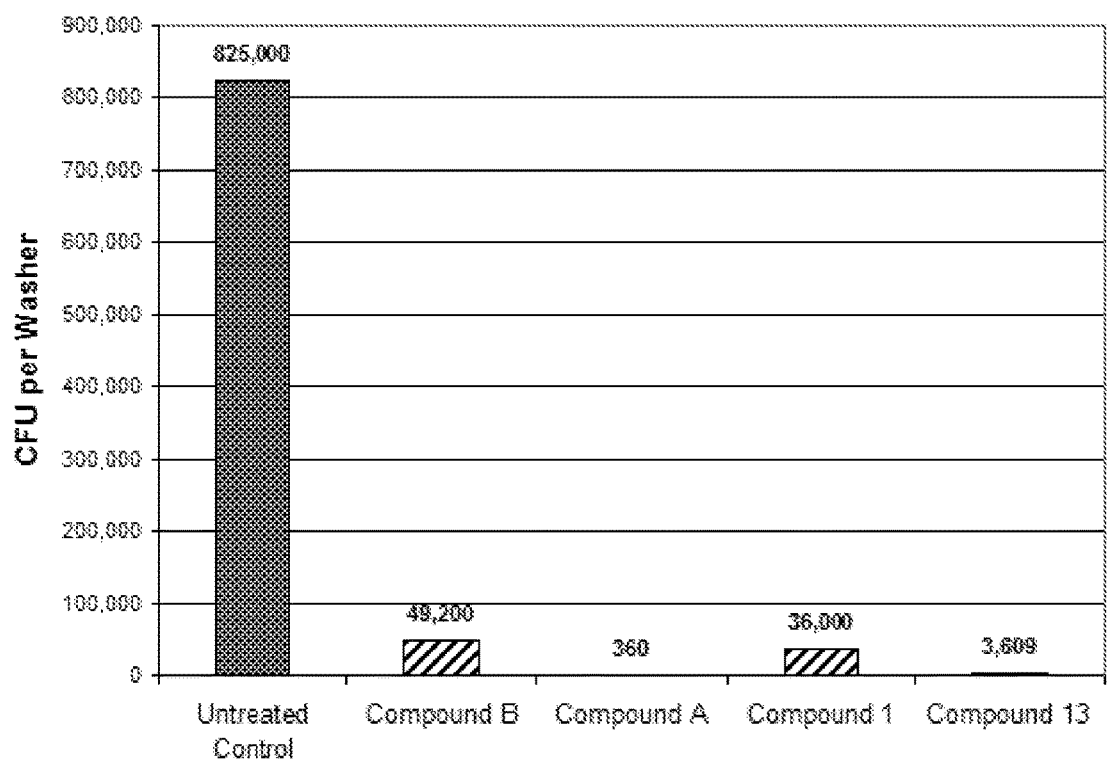
FIG. 6 graphically represents the biocide efficacy after 54 hours incubation against sessile organisms for the compounds of Formula (I), where the compounds tested are identified in Table 1. In the graph the vertical axis is the microbial population measured as CFU per washer, and the horizontal axis is the compound tested.
Figure 7:
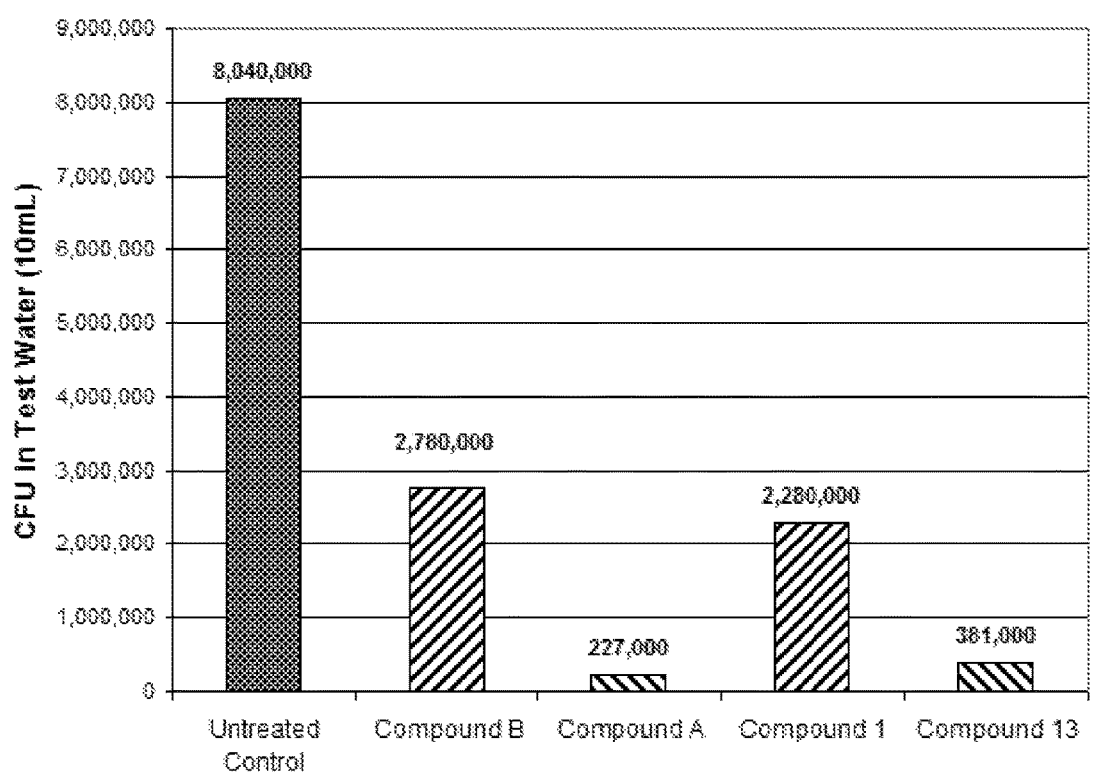
FIG. 7 graphically represents the biocide efficacy after 120 hours incubation against planktonic organisms for the compounds of Formula (I), where the compounds tested are identified in Table 1. In the graph the vertical axis is the microbial population measured as CFU in 10 mL of test water, and the horizontal axis is the compound tested.
Figure 8:
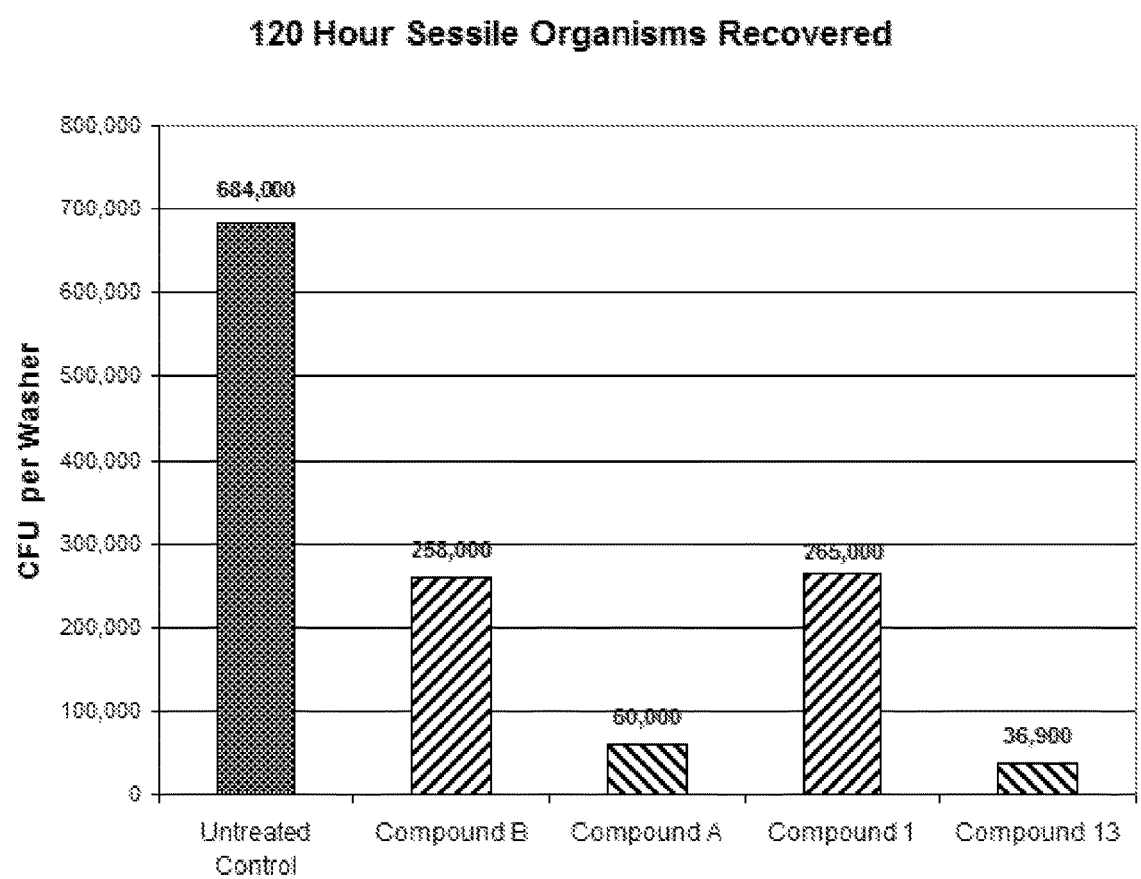
FIG. 8 graphically represents the biocide efficacy after 120 hours incubation against sessile organisms for the compounds of Formula (I), where the compounds tested are identified in Table 1. In the graph the vertical axis is the microbial population measured as CFU per washer, and the horizontal axis is the compound tested.

These data are shown graphically in FIG. 4 in terms of % inhibition.

The results in Table 7 for Compound B (32%) showed significant corrosion inhibition. 2-Hydroxypropane-1,2,3-tricarboxylic acid (9%) did not show significant amounts of inhibition. Compound 1 (54%) showed a high level of inhibition, and significantly more inhibition then Compound B or 2-hydroxypropane-1,2,3-tricarboxylic acid. Also Compound 1 showed greater than an additive effect than the sum of Compound B and 2-hydroxypropane-1,2,3-tricarboxylic acid. This result for Compound 1 of Formula (I), as with Compound 13, is an unexpected, surprising improvement. Concentrations in this set were 42 µM.

Biocidal Efficacy

An experiment was conducted to assess biocidal effectiveness of Compounds A and B and their respective Compounds 13 and 1 anion analogs. Time-kill tests were conducted using a hybrid planktonic-sessile procedure which allowed assessment of biocidal effectiveness against both planktonic and sessile microbial populations. A natural mixed aerobic microbial population in samples collected from an operating cooling tower was used as inoculum for the test. Biocide test concentration for Compound B was 10 ppm. All other products were tested at the equivalent molar concentration. Biocide exposure was 110 minutes.

The following procedure was used which generally followed the biocidal testing method of Walter, R. W. and Cooke, L. M., "2-(Decylthio)ethanamine Hydrochloride: A New Multifunctional Biocide Which Enhances Corrosion Inhibition," NACE Paper 410, 1997.

A water sample was collected from a cooling tower that contained a natural mixed population of microorganisms that grew at different rates when plated on Petrifilm. The populations of cells that grew on Petrifilm in 20-24 hours, 48 54 hours and at 120 hours were treated as separate populations.

Stainless steel washers (13 mm outside diameter with 5.5 mm inside diameter) were individually fastened to nylon fishing line, suspended in 900 mL of natural cooling tower water (CTW), and magnetically stirred at a gentle rate at room temperature. The washers were allowed seven days to develop a biofilm on their surface. Prior to chemical treatment, 10 mL aliquots of the CTW were removed from the beaker and placed into individual exposure test tubes along with a single washer.

Test compounds were then added to the individual tubes at equimolar concentrations. All exposure tests including untreated controls were conducted in triplicate (i.e., three washers in separate exposure tubes). After addition of the test compound, the tube was briefly mixed by mild vortexing and again occasionally throughout the exposure time.

Washer sonication to release organisms not released by the chemical treatment: After 120 minute exposure, the washer was removed from the tube, dipped 10 times in Letheen broth, then placed into a 9 mL tube of sterile Butterfields buffer, and sonicated for 8 minutes.

Determination of residual viable cell population in the bulk water: 1 mL of the water from the exposure tube was plated on petrifilm. A second 1 ml was added to 9 mL tube of Letheen broth and mixed by shaking 10 times. A 1 mL aliquot was plated on petrifilm, a second 1 mL aliquot was added to a 9 ml tube of Butterfields Broth and again shaken 10 times. This serial sequence of plating the dilution and subsequent 1/10 dilution was repeated through $10^{-4}$ to $10^{-5}$ dilution.

A 1 mL aliquot of the Letheen broth tube in which the washer was dipped 10× was plated onto petrifilm. A serial dilution of this Letheen wash tube was not performed in these studies, although it could have been done to determine how many CPU were rinsed from the washer in this mechanical wash step. It was assumed this tube would mainly be reflective of the planktonic organisms carried over by the CTW loosely adhering to the washer.

Determination of cell population removed from washers by sonication: After the tube with washer was sonicated, a 1 mL aliquot was plated onto petrifilm and a serial dilution in Butterfields Buffer was performed with each dilution being plated to petrifilm.

Determination of colony forming units (CFU) at different incubation times: After plating the various solutions on Petrifilm, the films were incubated at 36° C. for the first 24 hours. At 20 hours the Petrifilms were read and CFU were recorded. This population was defined as a fast growing population.

The Petrifilms were then incubated for additional time either at 36° C. or room temperature and read at 54 hours. This second population is in addition to the fast growth rate population and was defined as moderate growth rate organisms.

Incubation was continued and the Petrifilms read again after 120 hours. This third population was also treated as separate from the fast and moderate growth rate populations and is referred to as the slow growth rate population.

As noted above, each compound was evaluated in triplicate with three separate washers and the results were averaged. Average CFU/mL values were used to calculate total planktonic test population (CFU/10 mL) and total sessile test population (CFU/washer) in each test system.

Based on the results of these experiments we draw the following conclusions:

1. Exposure of the planktonic and sessile microbial populations in these tests to 10 ppm Compound B for 110 minutes resulted in moderate reductions in both populations (63% reduction in the total planktonic population, 80% reduction in the total sessile population).

2. Treatment with Compound 1 under the same experimental conditions and molar concentration yielded results very similar (within experimental error) to those obtained with Compound B, demonstrating that changing the anion of Compound B to dihydrogen 2-hydroxypropane-1,2,3-tricarboxylate has no measurable impact on the biocidal effectiveness of the parent Compound B molecule.

3. Treatment with Compound A under the same experimental conditions and molar concentration results in significantly greater reductions in planktonic and sessile microbial populations (97% and 96%, respectively).

4. Treatment with Compound 13 under the same experimental conditions and molar concentration yielded results very similar (within experimental error) to those obtained with Compound A, demonstrating that, similar to the case with Compound B, changing the anion of Compound A to dihydrogen 2-hydroxypropane-1,2,3-tricarboxylate has no measurable impact on the biocidal effectiveness of the parent Compound A molecule.

Results are shown in Table 8 below and graphically in FIGS. 5 through 8.

TABLE 8

|  | 20-24 h | % of Control | 48-54 h | % of Control | 120 h | % of Control | Total | % of Control |
|---|---|---|---|---|---|---|---|---|
| Planktonic CFU/10 mL | | | | | | | | |
| Untreated Control | 740 | | 377,000 | | 8,040,000 | | 8,410,000 | |
| Compound B | 810 | 81.7% | 320,000 | 85.0% | 2,780,000 | 34.6% | 3,100,000 | 36.8% |
| Compound A | 940 | 94.9% | 13,500 | 3.6% | 227,000 | 2.8% | 241,000 | 2.9% |
| Compound 1 | 970 | 97.9% | 340,000 | 90.3% | 2,280,000 | 28.4% | 2,620,000 | 31.1% |
| Compound 13 | 1110 | 112.0% | 111,000 | 29.5% | 381,000 | 4.7% | 493,000 | 5.9% |
| Sessile CFU/ | | | | | | | | |
| Untreated Control | 225 | | 825,000 | | 684,000 | | 1,510,000 | |
| Compound B | 207 | 92.8% | 49,200 | 6.0% | 258,000 | 37.7% | 307,000 | 20.3% |
| Compound A | 405 | 181.6% | 360 | 0.04% | 60,000 | 8.8% | 60,800 | 4.0% |
| Compound 1 | 234 | 104.9% | 36,000 | 4.4% | 265,000 | 38.7% | 301,000 | 19.9% |
| Compound 13 | 324 | 145.3% | 3,610 | 0.4% | 36,900 | 5.4% | 40,800 | 2.7% |

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

Accordingly, this description is to be construed as illustrative only and is for the purpose of teaching those skilled in the art the general manner of carrying out the invention.

What is claimed is:

1. A compound of the formula of Formula (IA) below:

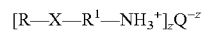

Formula (IA)

wherein:
R is a straight-chain or branched-chain $C_6$-$C_{24}$ alkyl or a straight-chain or branched-chain $C_6$-$C_{24}$ alkyloxy-$C_2$-$C_3$-alkyl;
X is S or O:
$R^1$ is a straight-chain or branched-chain $C_2$-$C_3$ alkyl;
z is a integer of at least 1 such that the compound of Formula (IA) is electrically neutral; and
Q is an anionic moiety derived from an acid having one or more acidic hydrogens, and has three or more groups capable of coordination to metal cations or electron-deficient sites on a metal surface, selected from the group consisting of the anions from: (1-hydroxyethan-1,1-diyl)bis(phosphonic acid);
provided that the compound of Formula (IA) is a solid wherein the compound of Formula (IA) is less soluble in water than its acid used to derive the Q anion.

2. The compound of claim 1 when X is S and Q is the anion derived from (1-hydroxyethan-1,1-diyl)bis(phosphonic acid).

3. The compound of claim 2 wherein the amine component is 2-(decylthio)ethanamine and Q is the anion derived from (1-hydroxyethan-1,1-diyl)bis(phosphonic acid).

4. The compound of claim 1 when X is O and Q is the anion derived from (1-hydroxyethan-1,1-diyl)bis(phosphonic acid).

5. The compound of claim 4 wherein the amine component is aminopropyloxydecane and Q is the anion derived from (1-hydroxyethan-1,1-diyl)bis(phosphonic acid).

* * * * *